United States Patent [19]

Yoshimura et al.

[11] Patent Number: 5,235,092
[45] Date of Patent: Aug. 10, 1993

[54] PHENOXYACETIC ACID DERIVATIVES AND PLANT GROWTH REGULATING AGENTS CONTAINING THEM AS ACTIVE INGREDIENTS

[75] Inventors: Takumi Yoshimura, Shizuoka; Tetsuo Takematsu; Makoto Konnai, both of Utsunomiya, all of Japan

[73] Assignees: Kumiai Chemical Industry Co., Ltd.; Ihara Chemical Industry Co., Ltd., both of Tokyo, Japan

[21] Appl. No.: 799,986

[22] Filed: Nov. 29, 1991

[30] Foreign Application Priority Data

Nov. 30, 1990 [JP] Japan .................................. 2-330167

[51] Int. Cl.⁵ ...................... C07C 69/76; C07C 59/48; A01N 37/38
[52] U.S. Cl. .................................... 504/190; 562/471; 562/621; 564/170; 564/175; 560/61; 504/317; 504/323; 504/338; 504/315; 504/110; 504/112
[58] Field of Search .................. 560/61; 562/471, 621; 564/170, 175; 71/109, 118

[56] References Cited

FOREIGN PATENT DOCUMENTS 2407148 8/1975 Fed. Rep. of Germany .

Primary Examiner—Paul J. Killos
Attorney, Agent, or Firm—Oblon, Spivak, McClelland, Maier & Neustadt

[57] ABSTRACT

A phenoxycetic acid derivative of the formula:

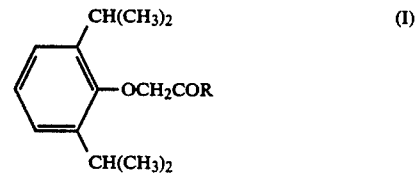

wherein R is a hydroxyl group, an alkoxy group, a group of the formula OM wherein M is an alkali metal ion, an alkaline earth metal ion, a transition metal ion, an ammonium ion or an organic ammonium ion, or a group of the formula $NHR_1$ wherein $R_1$ is a hydrogen atom, a hydroxyl group, an amino group, an allyloxy group or an ethoxycarboxylmethoxy group.

6 Claims, No Drawings

PHENOXYACETIC ACID DERIVATIVES AND PLANT GROWTH REGULATING AGENTS CONTAINING THEM AS ACTIVE INGREDIENTS

BACKGROUND OF THE INVENTION

1. Field of the Invention

The present invention relates to novel phenoxyacetic acid derivatives and plant growth regulating agents containing them as active ingredients.

2. Discussion of Background

It is known that certain phenoxyacetic acids having substitutents (particularly halogen atoms) on their phenyl rings and derivatives thereof exhibit plant growth regulating activities, and they are useful as herbicides (German Patent No. 1019234). Further, it is known that such plant growth regulating activities are strong particularly when at least one of ortho-positions on the phenyl rings is unsubstituted, and 2,6-di-substituted products usually show relatively weak activities only (J. Agr. Food Chem., 2(19), 996, (1954)). Further, a method for controlling growth of a plant is also known wherein a 2,6-di-substituted phenyl ring compound is employed (Japanese Unexamined Patent Publication No. 116639/1975). However, the plant growth regulating activities of the substance used here are not necessarily adequate.

SUMMARY OF THE INVENTION

The present inventors have synthesized various 2,6-di-substituted phenoxyacetic acid derivatives and studied their plant growth regulating activities. As a result, it has been found that novel 2,6-di-substituted phenoxyacetic acid derivatives having isopropyl groups at the 2- and 6-positions on the phenyl group, have excellent plant growth regulating activities, which are not observed with conventional phenoxyacetic acid derivatives. The present invention has been accomplished on the basis of this discovery.

Thus, the present invention provides a phenoxyacetic acid derivative of the formula:

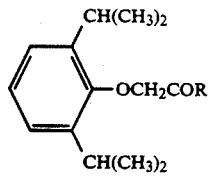

(I)

wherein R is a hydroxyl group, an alkoxy group, a group of the formula OM wherein M is an alkali metal ion, an alkaline earth metal ion, a transition metal ion, an ammonium ion or an organic ammonium ion, or a group of the formula $NHR_1$ wherein $R_1$ is a hydrogen atom, a hydroxyl group, an amino group, an allyloxy group or an ethoxycarboxylmethoxy group.

Now, specific examples of the compound of the present invention represented by the formula (I) will be shown in Table 1. However, it should be understood that the present invention is by no means restricted by such specific examples. The compound Nos. will be referred to in the subsequent description.

TABLE 1

Structure: 2,6-diisopropylphenyl-OCH$_2$COR

| Compound No. | R | Physical properties m.p. (°C.), or refractive index ($n_D^{20}$) |
|---|---|---|
| 1 | $OC_2H_5$ | 1.4876 |
| 2 | OH | 84–87 |
| 3 | $O^-.Na^+$ | >300 |
| 4 | $O^-.K^+$ | >300 |
| 5 | $O^-.\frac{1}{2}Ca^{++}$ | >300 |
| 6 | $O^-.\frac{1}{2}Cu^{++}$ | >300 |
| 7 | $O^-.(CH_3)_2CHNH_3^+$ | 154–159 |
| 8 | $O^-.CH_3NH_3^+$ | 130–135 |
| 9 | $O^-.(CH_3)_2NH_2^+$ | 169–173 |
| 10 | $O^-.(C_2H_5)_3NH^+$ | 1.5073 |
| 11 | $O^-.NH^+{}_2(CH_2CH_2OH)_2$ | 101–106 |
| 12 | $O^-.(CH_3)_3NC_2H_4OH^+$ | Not measurable |
| 13 | $NH_2$ | 136–138 |
| 14 | $NHNH_2$ | 85–87 |
| 15 | NHOH | 138–140 |
| 16 | $NHOCH_2CH=CH_2$ | 91–92 |
| 17 | $NHOCH_2COOC_2H_5$ | 1.4939 |

The compound of the formula (I) of the present invention can be prepared in accordance with the following methods (1) to (4). However, the preparation of the compound is not limited to such specific methods.

Reaction (1)

2,6-diisopropylphenol (II) + L—CH$_2$COR$^2$ (III) → 2,6-diisopropylphenyl-OCH$_2$COR$_2$ (I-1)

In the formulas, L is a halogen atom, a phenylsulfonyloxy group or a substituted phenylsulfonyloxy group, and $R^2$ is a hydroxyl group or an alkoxy group.

The compound of the formula (I-1) can be prepared by reacting 2,6-diisopropylphenol of the formula (II) and a compound of the formula (III) in the presence of at least 1 equivalent of a base in a suitable solvent within a range of from −20° C. to the boiling point of the solvent for from 0.5 to 24 hours, and acidifying the reaction solution after the reaction. When an inorganic base is used, a catalyst may be added if required for the reaction.

The base may be an alkali metal such as sodium metal or potassium metal, an alkali metal hydride or an alkaline earth metal hydride such as sodium hydride, potassium hydride or calcium hydride, an alkali metal alkoxide such as potassium t-butoxide, an alkali metal carbonate such as sodium carbonate or potassium carbonate, an alkali metal hydrogen carbonate such as sodium hydrogen carbonate or potassium hydrogen carbonate, an alkali metal hydroxide such as sodium hydroxide or potassium hydroxide, or an organic tertiary amine such as pyridine or triethylamine. The solvent may be a hydrocarbon solvent such as benzene, toluene or xylene, a halogenated hydrocarbon solvent such as methylene chloride or chloroform, an alcohol solvent such as t-butanol, an ether solvent such as diethyl ether, tetrahydrofuran or 1,4-dioxane, an ester solvent such as methyl acetate or ethyl acetate, a ketone solvent such as acetone or methyl ethyl ketone, an aprotic polar solvent such as N,N-dimethylformamide, N,N-dimethylacetamide or dimethyl sulfoxide, or other solvents such as acetonitrile and water. The catalyst may be potassium iodide or an onium compound such as benzyltriethyl ammonium chloride, or a polyglycol ether such as 18-crown-6-ether.

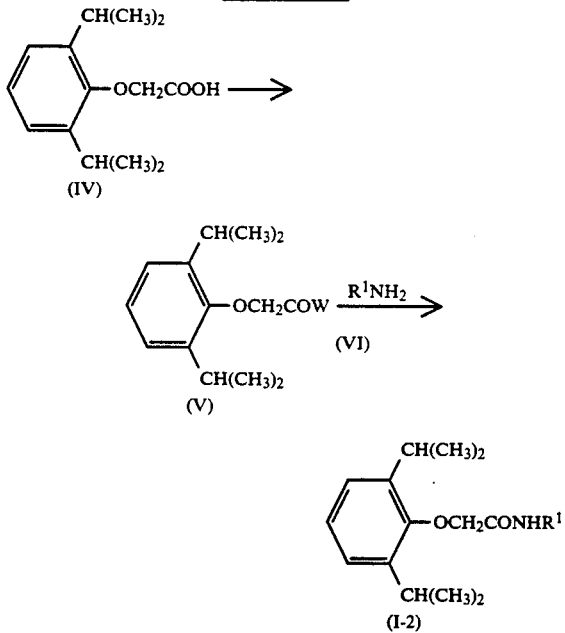

In the formulas, W is a halogen atom, and $R^1$ is as defined above.

The compound of the formula (I-2) can be prepared by reacting 2,6-diiospropylphenoxyacetic acid of the formula (IV) with a halogenating agent to convert it to an intermediate compound of the formula (V), and then reacting this compound with an amine of the formula (VI) in the presence of a base in a suitable solvent within a range of from $-20°$ C. to the boiling point of the solvent for from 0.5 to 24 hours.

The halogenating agent may be thionyl chloride, phosphorus pentachloride or phosphorus tribromide, and the base and the solvent may be the same as used in Reaction (1).

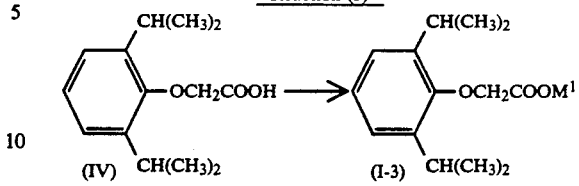

In the formula (I-3), $M^1$ is an alkali metal ion, an alkaline earth metal ion, an ammonium ion or an organic ammonium ion.

The compound of the formula (I-3) can be prepared by reacting 2,6-diisopropylphenoxyacetic acid of the formula (IV) with an equivalent amount of a base in a suitable solvent within a range of from room temperature to the boiling point of the solvent for from 0.5 to 24 hours.

The base may be an alkali metal hydroxide or an alkaline earth metal hydroxide such as sodium hydroxide or calcium hydroxide, an alkali metal carbonate or an alkaline earth metal carbonate such as sodium carbonate or calcium carbonate, an alkali metal hydride or an alkaline earth metal hydride such as sodium hydride, potassium hydride or calcium hydride, an alkali metal hydrogen carbonate such as sodium hydrogen carbonate or potassium hydrogen carbonate, ammonia or an organic amine such as isopropylamine. The solvent may be the same as used in Reaction (1).

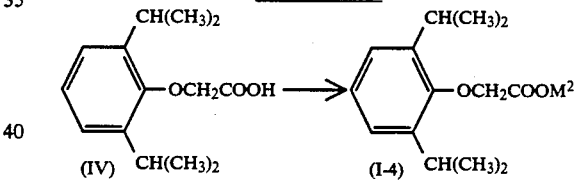

In the formula (I-4), $M^2$ is an alkaline earth metal ion or a transition metal ion.

The compound of the formula (I-4) can be prepared by reacting 2,6-diisopropylphenoxyacetic acid of the formula (IV) with an equivalent amount of an aqueous sodium hydroxide solution at room temperature, then adding a metal halide such as cupric chloride or calcium chloride, followed by a reaction in a solvent such as water or an alcohol at a temperature of from $-10°$ to $+200°$ C. for from one minute to 20 hours.

Now, the preparation of the compound of the present invention will be described in further detail with reference to Examples.

EXAMPLE 1

Preparation of 2,6-diisopropylphenoxyacetic acid (Compound 2)

16.4 g of 2,6-diisopropylphenol, 10.0 g of chloroacetic acid, 10.0 g of sodium hydroxide and 300 ml of water were put into a round bottom flask and stirred under reflux for 6 hours. The reaction mixture was cooled and then the pH was adjusted to from 3 to 4 with a dilute hydrochloric acid. The precipitate thereby formed was collected by filtration, washed with water and dried to obtain 20.5 g of crude crystals. The crude crystals were recrystallized from diethyl ether-hexane to obtain 19.6 g (yield: 88.3%) of the desired compound as colorless prism crystals. Melting point: 84°–87° C.

EXAMPLE 2

Preparation of ethyl 2,6-diisopropylphenoxyacetate (compound 1)

15.0 g of 2,6-diisopropylphenol, 10.3 g of potassium t-butoxide and 200 ml of N,N-dimethylformamide were put into a round bottom flask and stirred at room temperature for one hour. Then, to the reaction solution, 15.0 g of ethyl bromoacetate was added, and stirring was continued at room temperature. After reacting for three hours, 500 ml of water was added to the reaction solution, and the mixture was extracted twice with 200 ml of ethyl acetate. The extract was washed with water and dried over anhydrous magnesium sulfate overnight. After the drying, inorganic salts were separated by filtration, and the solvent was distilled off under reduced pressure to obtain 22.5 g of a liquid. The liquid was distilled under reduced pressure to obtain 22.0 g (yield: 96.1%) of the desired compound as a colorless liquid. Boiling point: 135°–137° C./1 mmHg. Refractive index ($n_D^{20}$) 1.4876.

EXAMPLE 3

Preparation of 2,6-diisopropylphenoxyacetamide (Compound 13)

8.5 g of 2,6-diisopropylphenoxyacetic acid and 4.8 g of thionyl chloride were put into a round bottom flask and stirred under heating at a temperature of from 60° to 70° C. for 2 hours. To the reaction solution, 50 ml of toluene was added, followed by concentration to remove excess thionyl chloride. Then, the concentrated solution was gradually added under cooling to a solution having 100 ml of acetone dissolved in 8 ml of aqueous ammonia of 25%. After stirring the mixture at room temperature for two hours, 300 ml of water was added to the reaction solution. The mixture was extracted twice with 100 ml of ethyl acetate. The extract was washed with water and then dried over anhydrous magnesium sulfate overnight. After the drying, inorganic salts were separated by filtration, and the solvent was distilled off under reduced pressure to obtain 6.8 g of crude crystals. The crude crystals were recrystallized from acetone-hexane to obtain 6.3 g of the desired compound as white powder (yield: 74.1%). Melting point: 136°–138° C.

EXAMPLE 4

Preparation of sodium salt of 2,6-diisopropylphenoxyacetic acid (Compound 3)

3.0 g of 2,6-diisopropylphenoxyacetic acid, 0.5 g of sodium hydroxide and 100 ml of toluene were put into a round bottom flask and stirred under reflux for 5 hours. The reaction solution was cooled, and then 100 ml of acetone was added thereto. The precipitate was collected by filtration, and the obtained crude crystals were washed with acetone and dried to obtain 2.1 g (yield: 63.6%) of the desired compound as white crystals of irregular shapes. Melting point: at least 300° C.

EXAMPLE 5

Preparation of calcium salt of 2,6-diisopropylphenoxyacetic acid (Compound 5)

3.0 g of 2,6-diisopropylphenoxyacetic acid and 50 ml of a 1.0% sodium hydroxide aqueous solution were put into a round bottom flask and stirred at room temperature for one hour. Then, 20 ml of a 4.0% calcium chloride aqueous solution was dropwise added thereto at room temperature. Stirring was continued at room temperature for one hour. Then, the formed precipitate was collected by filtration, washed with water and hexane and then dried to obtain 2.8 g of the desired compound as white powder (yield: 84.8%). Melting point: at least 300° C.

The plant growth regulating agent of the present invention comprises the phenoxyacetic acid derivative of the formula (I) as an active ingredient. When the compound of the present invention is to be applied to a paddy field, an upland field, an orchard, a non-agricultural field, etc. as a plant growth regulating agent, it may be used simply by diluting the active component with water or may be used in a suitable formulation, depending upon the particular purpose. In a usual case, the active ingredient is diluted by an inert liquid or solid carrier, and after incorporating a surfactant, a dispersant, an adjuvant, etc. as the case requires, formulated into various formulations such as dusts, wettable powders, emulsifiable concentrates and granules. The carrier to be used for such formulations may, for example, be a solid carrier such as Jeeklite, talc, bentonite, clay, kaolin, diatomaceous earth, fine silica powder, vermiculite, slaked lime, silica sand, ammonium sulfate or urea, or a liquid carrier such as isopropyl alcohol, xylene, cyclohexanone or methylnaphthalene. The surfactant and dispersant may, for example, be an alcohol-sulfuric acid ester, an alkylarylsulfonate, lignin sulfonate, polyoxyethylene glycol ether, polyoxy ethylene alkylaryl ether or polyoxyethylene sorbitan monoalkylate. The adjuvant may, for example, be carboxymethylcellulose, polyethylene glycol or gum arabic. In use, such a formulation may be diluted to a proper concentration before application, or may be directly applied. The compound of the present invention is applied in an amount of the active ingredient of from 0.1 g to 1 kg/10a or within a range of from 0.001 to 10,000 ppm as its concentration. Further, the compound of the present invention may be used in combination with an insecticide, a fungicide, a herbicide, other growth regulating agents or a fertilizer, as the case requires.

Now, the formulation method will be described in detail with reference to typical Formulation Examples. In the following Formulation Examples, "parts" means "parts by weight".

FORMULATION EXAMPLE 1

Wettable Powder

To 10 parts of Compound (3), 0.5 part of polyoxyethylenealkylarylether, 0.5 part of a sodium naphthalenesulfonate-formaline condensation product, 20 parts of diatomaceous earth and 69 parts of clay were mixed and pulverized to obtain a wettable powder.

FORMULATION EXAMPLE 2

Wettable Powder

To 10 parts of compound (3), 0.5 part of polyoxyethylenealkylarylether, 0.5 part of a sodium naphthalenesulfonate-formaline condensation product, 20 parts of diatomaceous earth, 5 parts of Carprex 80 and 64 parts of clay were mixed and pulverized to obtain a wettable powder.

FORMULATION EXAMPLE 2

Emulsifiable Concentrate

To 30 parts of Compound (2), 60 parts of a mixture of equivalent amounts of xylene and isophorone and 10 parts of a mixture of a polyoxyethylenealkylarylether polymer and an alkylbenzenesufonic acid metal salt were added and thoroughly mixed to obtain an emulsifiable concentrate.

FORMULATION EXAMPLE 4

Granule

Ten parts by water was added to 10 parts of Compound (2), 80 parts of a filler prepared by mixing talc and bentonite at a ratio of 1:3, 5 parts of fine silica powder, and 5 parts of a mixture of a polyoxyethylenealkylarylether polymer and an alkylbenzenesufonic acid metal salt, and the mixture was thoroughly kneaded to obtain a paste. The paste was then extruded through sieve openings having a diameter of 0.7 mm and dried and then cut into a length of from 0.5 to 1 mm to obtain a granule.

The compound of the formula (I) of the present invention gives remarkable effects to the physiological reactions or to the growth processes of plants and thus is useful for various plant growth regulating agents. The performance of the plant growth regulating activities is determined by the compound, the concentration, the type of the plant or the growth stage of the plant. A part of such a variety of activities is similar to the action of gibberellin as a plant hormone. Further, such activities are observed even at a low concentration. It is advantageous that even when used at a high concentration, it shows no phytotoxicity to plants and thus can safely be used.

The major plant growth regulating activities of the compound of the present invention are as follows:

(1) For many plants, it increases formation of the roots, or promotes the growth of roots.

(2) It promotes the growth of foliages, promotes the internode elongation, or increases the number of leaves.

(3) It promotes flowering, or increases the number of flowers.

(4) It promotes fruit bearing, increases the number of fruits, or promotes enlargement of fruits.

(5) It improves the germination percentage of seeds or bulbs, or promotes the germination.

(6) It induces parthenocarpy of fruit trees.

(7) It reduces the phytotoxicity of a herbicide against crop plants.

The compound of the present invention exhibiting such plant growth regulating activities can be used as a rooting or root-forming agent, a seeding-culturing agent, a growth-promoting agent, a flowering-promoting agent, a hervest-increasing agent, a fruit-bearing-promoting agent, a fruit-enlargement-promoting agent or a fruiting-promoting agent.

Now, the plant growth regulating agent of the present invention will be described with reference to Test Examples. However, it should be understood that the present invention is by no means restricted to such specific Test Examples.

TEST EXAMPLE 1

Foliage-Growth Promoting Effects (Morning Glory)

Into a polypropylene pot having an inner diameter of 12 cm, sieved upland field soil was filled, and seeds of Japanese morning glory (*Pharbitis nil*) (variety: Mizuumi) were sown and covered with soil in a thickness of 1 cm, and then they were cultured under irradiation with light for 14 hours. Then, when the second foliage leaf started to grow, a cotton thread was passed through an upper portion of the hypocotyl, and one end of the cotton thread was dipped in a solution of a test compound having a predetermined concentration (5 ml), and the growth promoting effects were examined upon expiration of 60 days. The results are shown in Table 2.

TABLE 2

| Compound No. | Concentration (ppm) | Length of the aerial part (cm) | |
|---|---|---|---|
| | | Test I | Test II |
| 3 | 0.001 | 78 | 93 |
| | 0.003 | 119 | 134 |
| | 0.01 | 153 | 141 |
| | 0.03 | 149 | 131 |
| | 0.1 | 97 | 119 |
| | 0.3 | 127 | 103 |
| | 1.0 | 96 | 107 |
| | 3.0 | 146 | 126 |
| | 10.0 | 109 | 114 |
| | 30.0 | 132 | 128 |
| Not treated | | 46 | 52 |

TEST EXAMPLE 2

Foliage and Root-Growth Promoting Effects (Rice)

A sheet of filter paper was put in a Petri dish having an inner diameter of 5 cm, and 5 ml of a solution of a test compound of a predetermined concentration was poured thereto, and seven germinated seeds of rice (*Oryza sativa*) (variety: Akinishiki) were put on the filter paper. The material was left to stand at room temperature for 15 days (from May 30 to June 14), whereupon the growth promoting activities were examined. The results are shown in Table 3.

TABLE 3

| Compound No | Concentration (ppm) | Average length of the aerial part (cm) | Average length of root part (cm) |
|---|---|---|---|
| 3 | 0.1 | 6.81 | 14.57 |
| | 0.3 | 6.86 | 14.75 |
| | 1.0 | 7.23 | 15.93 |
| | 3.0 | 6.90 | 17.09 |
| | 10.0 | 7.01 | 20.80 |
| | 30.0 | 7.65 | 16.20 |
| | 100.0 | 9.16 | 15.37 |
| Not treated | | 6.83 | 14.65 |

TEST EXAMPLE 3

Flowering-Promoting and Flower-Increasing Effects

In a propylene pot having an inner diameter of 12 cm, upland field soil was filled, and seeds of morning glory (*Pharbitis nil*), cucumber (*Cucumis sativus*), azuki bean (*Phaseolus angularis*) and garden zinnia (*Zinna elegans.*) were sown (one pot for each type of seeds) and covered with soil in a thickness of 1 cm, and they were cultured under irradiation with light for 14 hours. Then, when the second foliage leaves started to grow, a cotton thread was passed through an upper portion of each hypocotyl, and one end of the cotton thread was dipped in a solution of a test compound having a predetermined concentration (5 ml), whereupon the number of days from the treatment to the flowering and the number of flowers were examined (final examination date: 70th day after the treatment). The results are shown in Table 4 [morning glory (variety: Mizuumi)], Table 5 (cucumber), Table 6 (azuki bean) and Table 7 (garden zinnia).

TABLE 4

| Compound No. | Concentration (ppm) | Number of days from treatment to flowering | | Number of flowers | |
|---|---|---|---|---|---|
| | | Test I | Test II | Test I | Test II |
| 3 | 0.001 | 43 | 43 | 11 | 10 |
| | 0.003 | 43 | 42 | 14 | 12 |
| | 0.01 | 42 | 42 | 12 | 12 |
| | 0.03 | 44 | 43 | 12 | 13 |
| | 0.1 | 42 | 43 | 13 | 12 |
| | 0.3 | 43 | 43 | 10 | 10 |
| | 1.0 | 42 | 44 | 14 | 12 |
| | 3.0 | 42 | 45 | 11 | 13 |
| | 10.0 | 43 | 44 | 12 | 11 |
| Not treated | | 61 | 60 | 4 | 6 |

TABLE 5

| Compound No. | Concentration (ppm) | Number of days from treatment to flowering | | Number of flowers | |
|---|---|---|---|---|---|
| | | Test I | Test II | Test I | Test II |
| 3 | 0.001 | 24 | 23 | 8 | 9 |
| | 0.003 | 24 | 23 | 9 | 10 |
| | 0.01 | 23 | 24 | 8 | 10 |
| | 0.03 | 23 | 23 | 7 | 9 |
| | 0.1 | 23 | 23 | 8 | 8 |
| | 0.3 | 24 | 24 | 11 | 9 |
| | 1.0 | 23 | 23 | 10 | 9 |
| | 3.0 | 25 | 23 | 9 | 10 |
| | 10.0 | 24 | 24 | 9 | 9 |
| | 30.0 | 23 | 25 | 8 | 9 |
| Not treated | | 42 | 43 | 2 | 3 |

TABLE 6

| Compound No. | Concentration (ppm) | Number of days from treatment to flowering | | Number of flowers | |
|---|---|---|---|---|---|
| | | Test I | Test II | Test I | Test II |
| 3 | 0.001 | 25 | 25 | 5 | 5 |
| | 0.003 | 25 | 25 | 6 | 6 |
| | 0.01 | 26 | 25 | 5 | 6 |
| | 0.03 | 25 | 25 | 5 | 5 |
| | 0.1 | 27 | 26 | 6 | 6 |
| | 0.3 | 25 | 25 | 5 | 7 |
| | 1.0 | 25 | 26 | 6 | 5 |
| | 3.0 | 25 | 25 | 5 | 6 |
| | 10.0 | 25 | 25 | 5 | 5 |
| | 30.0 | 25 | 25 | 5 | 6 |
| Not treated | | 30 | 30 | 5 | 5 |

TABLE 7

| Compound No. | Concentration (ppm) | Number of days from treatment to flowering | | Number of flowers | |
|---|---|---|---|---|---|
| | | Test I | Test II | Test I | Test II |
| 3 | 0.001 | 31 | 32 | 1 | 1 |
| | 0.003 | 32 | 33 | 1 | 1 |
| | 0.01 | 33 | 31 | 1 | 1 |
| | 0.03 | 32 | 33 | 1 | 1 |
| | 0.1 | 34 | 35 | 1 | 1 |
| | 0.3 | 33 | 35 | 1 | 1 |
| | 1.0 | 31 | 35 | 1 | 1 |
| | 3.0 | 33 | 32 | 1 | 1 |
| | 10.0 | 33 | 31 | 1 | 1 |
| | 30.0 | 36 | 34 | 1 | 1 |
| Not treated | | 51 | 57 | 1 | 1 |

TEST EXAMPLE 4

*Sagittaria pygmaea* Flowering-Promoting Effects

Into a porcelain pot having an inner diameter of 12 cm, puddled paddy field soil was filled, and germinated two tubers of *Sagittaria pygmaea* per pot were transplanted, and water was introduced to a depth of 3 cm. Next day, an aqueous solution of a test compound having a predetermined concentration was dropped to the water for treatment, whereupon the presence or absence of flowering of *Sagittaria pygmaea* and the number of days till flowering were examined (final examination day: 50th day after the treatment). The results are shown in Table 8.

TABLE 8

| Compound No. | Concentration (g/10a) | Flowering (Yes: ○, No: x) | Average number of days till flowering (days) |
|---|---|---|---|
| 1 | 12.5 | x | — |
| | 25 | ○ | 35 |
| | 50 | ○ | 32 |
| | 100 | ○ | 40 |
| | 200 | ○ | 37 |
| | 400 | ○ | 33 |
| 2 | 12.5 | x | — |
| | 25 | ○ | 38 |
| | 50 | ○ | 38 |
| | 100 | ○ | 30 |
| | 200 | ○ | 31 |
| | 400 | ○ | 36 |
| 3 | 12.5 | ○ | 39 |
| | 25 | ○ | 37 |
| | 50 | ○ | 32 |
| | 100 | ○ | 31 |
| | 200 | ○ | 34 |
| | 400 | ○ | 30 |
| 13 | 12.5 | x | — |
| | 25 | x | — |
| | 50 | x | — |
| | 100 | x | — |
| | 200 | ○ | 37 |
| | 400 | ○ | 33 |
| 15 | 12.5 | x | — |
| | 25 | x | — |
| | 50 | ○ | 37 |
| | 100 | ○ | 32 |
| | 200 | ○ | 31 |
| | 400 | ○ | 33 |
| 16 | 12.5 | x | — |
| | 25 | x | — |
| | 50 | ○ | 36 |
| | 100 | ○ | 40 |
| | 200 | ○ | 31 |
| | 400 | ○ | 35 |
| 17 | 12.5 | ○ | 39 |
| | 25 | ○ | 37 |
| | 50 | ○ | 35 |
| | 100 | ○ | 38 |
| | 200 | ○ | 33 |
| | 400 | ○ | 3 |
| Not treated | | x | — |

What is claimed is:

1. A phenoxyacetic acid derivative of the formula:

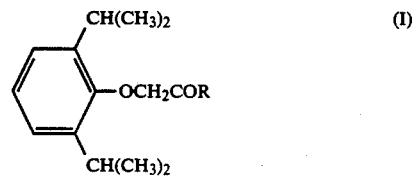

(I)

wherein R is a hydroxyl group, an alkoxy group, a group of the formula OM wherein M is an alkali metal ion, an alkaline earth metal ion, a transition metal ion, an ammonium ion or an organic ammonium ion, or a group of the formula $NHR_1$ wherein $R_1$ is a hydrogen atom, a hydroxyl group, an amino group, an allyloxy group or an ethoxycarboxylmethoxy group.

2. The phenoxyacetic acid derivative according to claim 1, wherein R in the formula (I) is $OC_2H_5$, OH, $O^-.Na^+$, $O^-.K^+$, $O^-.1/2Ca^{++}$, $O^-.1/2Cu^{++}$, $O^-.(CH_3)_2CHNH_3$, $O^-.CH_3NH_3$, $O^-.(CH_3)_2NH_2$, $O^-.(C_2H_5)_3NH$, $O^-.NH^+_2(CH_2CH_2OH)_2$, $O^-.(CH_3)_3NC_2H_4OH$, $NH_2$, $NHNH_2$, NHOH, $NHOCH_2CH=CH_2$ or $NHOCH_2COOC_2H_5$.

3. A plant growth regulating agent comprising an effective amount of a phenoxyacetic acid derivative of the formula:

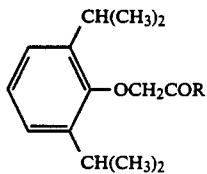

wherein R is a hydroxyl group, an alkoxy group, a group of the formula OM wherein M is an alkali metal ion, an alkaline earth metal ion, a transition metal ion, an ammonium ion or an organic ammonium ion, or a group of the formula $NHR_1$ wherein $R_1$ is a hydrogen atom, a hydroxyl group, an amino group, an allyloxy group or an ethoxycarboxylmethoxy group, and an agricultural carrier or diluent.

4. The plant growth regulating agent according to claim 1, wherein R in the formula (I) is $OC_2H_5$, OH, $O^-.Na^+$, $O^-.K^+$, $O^-.1/2Ca^{++}$, $O^-.1/2Cu^{++}$, $O^-.(CH_3)_2CHNH_3$, $O^-.CH_3NH_3$, $O^-.(CH_3)_2NH_2$, $O^-.(C_2H_5)_3NH$, $O^-.NH^+_2(CH_2CH_2OH)_2$, $O^-.(CH_3)_3NC_2H_4OH$, $NH_2$, $NHNH_2$, NHOH, $NHOCH_2CH=CH_2$ or $NHOCH_2COOC_2H_5$.

5. A method for controlling growth of a plant, which comprises applying an effective amount of a phenoxyacetic acid derivative of the formula:

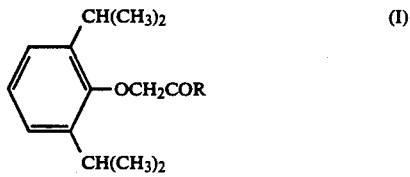

wherein R is a hydroxyl group, an alkoxy group, a group of the formula OM wherein M is an alkali metal ion, an alkaline earth metal ion, a transition metal ion, an ammonium ion or an organic ammonium ion, or a group of the formula $NHR_1$ wherein $R_1$ is a hydrogen atom, a hydroxyl group, an amino group, an allyloxy group or an ethoxycarboxylmethoxy group, to the plant.

6. The method according to claim 5, wherein R in the formula (I) is $OC_2H_5$, OH, $O^-.Na^+$, $O^-.K^+$, $O^-.1/2Ca^{++}$, $O^-.1/2Cu^{++}$, $O^-.(CH_3)_2CHNH_3$, $O^-.CH_3NH_3$, $O^-.(CH_3)_2NH_2$, $O^-.(C_2H_5)_3NH$, $O^-.NH^+_2(CH_2CH_2OH)_2$, $O^-.(CH_3)_3NC_2H_4OH$, $NH_2$, $NHNH_2$, NHOH, $NHOCH_2CH=CH_2$ or $NHOCH_2COOC_2H_5$.

* * * * *